United States Patent [19]

Buss et al.

[11] Patent Number: 4,721,694

[45] Date of Patent: * Jan. 26, 1988

[54] PLATINUM-BARIUM-TYPE L ZEOLITE

[75] Inventors: Waldeen C. Buss, Kensington; Thomas R. Hughes, Orinda, both of Calif.

[73] Assignee: Chevron Research Company, San Francisco, Calif.

[*] Notice: The portion of the term of this patent subsequent to Jan. 26, 2005 has been disclaimed.

[21] Appl. No.: 889,977

[22] Filed: Jul. 24, 1986

Related U.S. Application Data

[60] Division of Ser. No. 405,837, Aug. 6, 1982, Pat. No. 4,634,518, which is a continuation-in-part of Ser. No. 344,570, Feb. 1, 1982, abandoned.

[51] Int. Cl.$^4$ ............................................. B01J 29/32
[52] U.S. Cl. ........................................ 502/66; 502/74
[58] Field of Search .................. 502/66, 74; 208/138

[56] References Cited

U.S. PATENT DOCUMENTS

| | | | |
|---|---|---|---|
| 2,783,123 | 1/1974 | Young | 208/111 |
| 3,397,137 | 8/1968 | Pickert et al. | 208/138 |
| 4,104,320 | 8/1978 | Bernard et al. | 260/673.5 |
| 4,268,702 | 5/1981 | Duprez et al. | 208/138 |
| 4,325,808 | 4/1982 | Kim et al. | 208/65 |
| 4,443,326 | 4/1984 | Field | 208/138 |
| 4,478,706 | 10/1984 | Cohen | 208/138 |
| 4,517,306 | 5/1985 | Buss | 502/66 |
| 4,595,670 | 6/1986 | Tauster et al. | 502/66 |

FOREIGN PATENT DOCUMENTS

| | | |
|---|---|---|
| 895280 | 3/1972 | Canada . |
| 981094 | 1/1965 | United Kingdom . |
| 1074129 | 6/1967 | United Kingdom . |
| 1161071 | 8/1969 | United Kingdom . |
| 1183000 | 3/1970 | United Kingdom . |
| 1497526 | 1/1978 | United Kingdom . |

OTHER PUBLICATIONS

J. R. Bernard, "Hydrocarbons Aromatization on Platinum Alkaline Zeolites", Proceed. 5th Int'l Conf. on Zeolites, 686–695 (1980).

*Primary Examiner*—Carl F. Dees
*Attorney, Agent, or Firm*—S. R. La Paglia; T. G. DeJonghe; P. L. McGarrigle, Jr.

[57] ABSTRACT

A new catalyst is disclosed which is useful for dehydrocyclizing alkanes. This catalyst contains a type L zeolite, a Group VIII metal, and an alkaline earth metal. Preferably, this catalyst contains a type L zeolite, from 0.1% to 5% by weight platinum and from 1% to 20% by weight barium.

19 Claims, No Drawings

PLATINUM-BARIUM-TYPE L ZEOLITE

CROSS-REFERENCE TO RELATED APPLICATION

This is a division of application Ser. No. 405,837, filed Aug. 6, 1982 now U.S. Pat. No. 4,634,518 which is a continuation-in-part of application Ser. No. 344,570, filed Feb. 1, 1982 and now abandoned.

BACKGROUND OF THE INVENTION

The invention relates to a new catalyst and a method using that catalyst in reforming hydrocarbons, more particularly dehydrocyclizing acyclic hydrocarbons containing at least 6 carbon atoms, to form the corresponding aromatic hydrocarbons.

Catalytic reforming is well known in the petroleum industry and refers to the treatment of naphtha fractions to improve the octane rating by the production of aromatics. The more important hydrocarbon reactions occurring during reforming operation include dehydrogenation of cyclohexanes to aromatics, dehydroisomerization of alkylcyclopentanes to aromatics, and dehydrocyclization of acyclic hydrocarbons to aromatics. A number of other reactions also occur, including the following: dealkylation of alkylbenzenes, isomerization of paraffins, and hydrocracking reactions which produce light gaseous hydrocarbons, e.g., methane, ethane, propane and butane. Hydrocracking reactions are to be particularly minimized during reforming as they decrease the yield of gasoline boiling products and hydrogen.

Because of the demand for high octane gasoline for use as motor fuels, etc., extensive research is being devoted to the development of improved reforming catalysts and catalytic reforming processes. Catalysts for successful reforming processes must possess good selectivity, i.e., be able to produce high yields of liquid products in the gasoline boiling range containing large concentrations of high octane number aromatic hydrocarbons and accordingly, low yields of light gaseous hydrocarbons. The catalysts should possess good activity in order that the temperature required to produce a certain quality product need not be too high. It is also necessary that catalysts either possess good stability in order that the activity and selectively characteristics can be retained during prolonged periods of operation, or be sufficiently regenerable to allow frequent regeneration without loss of performance.

Catalysts comprising platinum, for example, platinum supported on alumina, are well known and widely used for reforming of naphthas. The most important products of catalytic reforming are benzene and alkylbenzenes. These aromatic hydrocarbons are of great value as high octane number components of gasoline.

Catalytic reforming is also an important process for the chemical industry because of the great and expanding demand for aromatic hydrocarbons for use in the manufacture of various chemical products such as synthetic fibers, insecticides, adhesives, detergents, plastics, synthetic rubbers, pharmaceutical products, high octane gasoline, perfumes, drying oils, ion-exchange resins, and various other products well known to those skilled in the art. One example of this demand is in the manufacture of alkylated aromatics such as ethylbenzene, cumene and dodecylbenzene by using the appropriate mono-olefins to alkylate benzene. Another example of this demand is in the area of chlorination of benzene to give chlorobenzene which is then used to prepare phenol by hydrolysis with sodium hydroxide. The chief use for phenol is in the manufacture of phenol-formaldehyde resins and plastics. Another route to phenol uses cumene as a starting material and involves the oxidation of cumene by air to cumene hydroperoxide which can then be decomposed to phenol and acetone by the action of an appropriate acid. The demand for ethylbenzene is primarily derived from its use to manufacture styrene by selective dehydrogenation; styrene is in turn used to make styrene-butadiene rubber and polystyrene. Ortho-xylene is typically oxidized to phthalic anhydride by reaction in vapor phase with air in the presence of a vanadium pentoxide catalyst. Phthalic anhydride is in turn used for production of plasticizers, polyesters and resins. The demand for para-xylene is caused primarily by its use in the manufacture of terephthalic acid or dimethylterephthalate which in turn is reacted with ethylene glycol and polymerized to yield polyester fibers. Substantial demand for benzene also is associated with its use to produce aniline, Nylon, maleic anhydride, solvents and the like petrochemical products. Toluene, on the other hand, is not, at least relative to benzene and the $C_8$ aromatics, in great demand in the petrochemical industry as a basic building block chemical; consequently, substantial quantities of toluene are hydrodealkylated to benzene or disproportionated to benzene and xylene. Another use for toluene is associated with the transalkylation of trimethylbenzene with toluene to yield xylene.

Responsive to this demand for these aromatic products, the art has developed and industry has utilized a number of alternative methods to produce them in commercial quantities. One response has been the construction of a significant number of catalytic reformers dedicated to the production of aromatic hydrocarbons for use as feedstocks for the production of chemicals. As in the case with most catalytic processes, the principal measure of effectiveness for catalytic reforming involves the ability of the process to convert the feedstocks to the desired products over extended periods of time with minimum interference of side reactions.

The dehydrogenation of cyclohexane and alkylcyclohexanes to benzene and alkylbenzenes is the most thermodynamically favorable type of aromatization reaction of catalytic reforming. This means that dehydrogenation of cyclohexanes can yield a higher ratio of (aromatic product/nonaromatic reactant) than either of the other two types of aromatization reactions at a given reaction temperature and pressure. Moreover, the dehydrogenation of cyclohexanes is the fastest of the three aromatization reactions. As a consequence of these thermodynamic and kinetic considerations, the selectivity for the dehydrogenation of cyclohexanes is higher than that for dehydroisomerization or dehydrocyclization. Dehydroisomerization of alkylcyclopentanes is somewhat less favored, both thermodynamically and kinetically. Its selectivity, although generally high, is lower than that for dehydrogenation. Dehydrocyclization of paraffins is much less favored both thermodynamically and kinetically. In conventional reforming, its selectivity is much lower than that for the other two aromatization reactions.

The selectivity disadvantage of paraffin dehydrocyclization is particularly large for the aromatization of compounds having a small number of carbon atoms per molecule. Dehydrocyclization selectivity in conventional reforming is very low for $C_6$ hydrocarbons. It increases with the number of carbon atoms per molecule, but remains substantially lower than the aromatization selectivity for dehydrogenation or dehydroisomerization of naphthenes having the same number of carbon atoms per molecule. A major improvement in the catalytic reforming process will require, above all else, a drastic improvement in dehydrocyclization selectivity that can be achieved while maintaining adequate catalyst activity and stability.

In the dehydrocyclization reaction, acyclic hydrocarbons are both cyclized and dehydrogenated to produce aromatics. The conventional methods of performing these dehydrocyclization reactions are based on the use of catalysts comprising a noble metal or a carrier. Known catalysts of this kind are based on alumina carrying 0.2% to 0.8% by weight of platinum and preferably a second auxiliary metal.

A disadvantage of conventional naphtha reforming catalysts is that with $C_6$-$C_8$ paraffins, they are usually more selective for other reactions (such as hydrocracking) than they are for dehydrocyclization. A major advantage of the catalyst of the present invention is its high selectivity for dehydrocyclization.

The possibility of using carriers other than alumina has also been studied and it was proposed to use certain molecular sieves such as X and Y zeolites, which have pores large enough for hydrocarbons in the gasoline boiling range to pass through. However, catalysts based upon these molecular sieves have not been commercially successful.

In the conventional method of carrying out the aforementioned dehydrocyclization, acyclic hydrocarbons to be converted are passed over the catalyst, in the presence of hydrogen, at temperatures of the order of 500° C. and pressures of from 5 to 30 bars. Part of the hydrocarbons are converted into aromatic hydrocarbon, and the reaction is accompanied by isomerization and cracking reactions which also convert the paraffins into isoparaffins and lighter hydrocarbons.

The rate of conversion of the acyclic hydrocarbons into aromatic hydrocarbons varies with the number of carbon atoms per reactant molecule, reaction conditions and the nature of the catalyst.

The catalysts hitherto used have given moderately satisfactory results with heavy paraffins, but less satisfactory results with $C_6$-$C_8$ paraffins, particularly $C_6$ paraffins. Catalysts based on a type L zeolite are more selective with regard to the dehydrocyclization reaction; can be used to improve the rate of conversion to aromatic hydrocarbons without requiring higher temperatures than those dictated by thermodynamic considerations (higher temperatures usually have a considerable adverse effect on the stability of the catalyst); and produce excellent results with $C_6$-$C_8$ paraffins, but catalysts based on type L zeolite have not achieved commercial usage, apparently because of inadequate stability.

In one method of dehydrocyclizing aliphatic hydrocarbons, hydrocarbons are contacted in the presence of hydrogen with a catalyst consisting essentially of a type L zeolite having exchangeable cations of which at least 90% are alkali metal ions selected from the group consisting of ions of lithium, sodium, potassium, rubidium and cesium and containing at least one metal selected from the group which consists of metals of Group VIII of the Periodic Table of Elements, tin and germanium, said metal or metals including at least one metal from Group VIII of said Periodic Table having a dehydrogenating effect, so as to convert at least part of the feedstock into aromatic hydrocarbons.

A particularly advantageous embodiment of this method is a platinum/alkali metal/type L zeolite catalyst containing cesium or rubidium because of its excellent activity and selectivity for converting hexanes and heptanes to aromatics, but stability remains a problem.

SUMMARY OF THE INVENTION

The present invention overcomes the deficiencies of the prior art by using a catalyst comprising a type L zeolite, an alkaline earth metal selected from the group consisting of barium, strontium and calcium and a Group VIII metal to reform hydrocarbons. This catalyst gives superior selectivity for converting acyclic hydrocarbons to aromatics than shown in prior art processes. This catalyst also gives satisfactory run length. The hydrocarbons are contacted with a catalyst comprising a type L zeolite, at least one Group VIII metal (preferably platinum); and an alkaline earth metal selected from the group consisting of barium, strontium and calcium (preferably barium).

Preferably, the catalyst contains: (a) a type L zeolite containing from 0.1% to 5% by weight platinum (preferably from 0.1% to 1.5% by weight platinum) and 0.1% to 40% by weight barium (preferably from 0.1% to 35% by weight barium, more preferably from 1% to 20% by weight barium); and (b) an inorganic binder. The majority of the type L zeolite crystals are preferably greater than 500 Angstoms, more preferably greater than 1000 Angstroms. In the most preferred embodiment, at least 80% of the crystals of type L zeolite are greater than 1000 Angstoms. The inorganic binder is preferably either a silica, alumina, an aluminosilicate or a clay. The hydrocarbons are contacted with the barium-exchanged type zeolite at a temperature of from 400° C. to 600° C. (preferably 450° C. to 550° C.); an LHSV of from 0.1 to 10 (preferably from 0.3 to 5); a pressure of from 1 atmosphere to 500 psig (preferably from 50 to 200 psig); and an $H_2$/HC ratio of from 0 to 20:1 (preferably from 2:1 to 6:1).

DESCRIPTION OF THE PREFERRED EMBODIMENTS

In its broadest aspect, the present invention involves a catalyst comprising a type L zeolite, an alkaline earth metal and a Group VIII metal and its use in the reforming of hydrocarbons, in particular, the dehydrocyclization of acyclic hydrocarbons at a high selectivity.

The term "selectivity" as used in the present invention is defined as the percentage of moles of acyclic hydrocarbons converted to aromatics relative to moles converted to aromatics and cracked products, i.e., Selectivity = $\dfrac{100 \times \text{moles of acyclic hydrocarbons converted to aromatics}}{\text{moles of acyclic hydrocarbons converted to aromatics and cracked products}}$ Isomerization of paraffins and interconversion of paraffins and alkylcyclopentanes having the same number of carbon atoms per molecule are not considered in determining selectivity.

The term "selectivity for n-hexane" as used in the present invention is defined as the percentage of moles of n-hexane converted to aromatics relative to moles converted to aromatics and cracked products.

The selectivity for converting acyclic hydrocarbons to aromatics is a measure of the efficiency of the process in converting acyclic hydrocarbons to the desired and valuable products: aromatics and hydrogen, as opposed to the less desirable products of hydrocracking.

Highly selective catalysts produce more hydrogen than less selective catalysts because hydrogen is produced when acyclic hydrocarbons are converted to aromatics and hydrogen is consumed when acyclic hydrocarbons are converted to cracked products. Increasing the selectivity of the process increases the amount of hydrogen produced (more aromatization) and decreases the amount of hydrogen consumed (less cracking).

Another advantage of using highly selective catalysts is that the hydrogen produced by highly selective catalysts is purer than that produced by less selective catalysts. This higher purity results because more hydrogen is produced, while less low boiling hydrocarbons (cracked products) are produced. The purity of hydrogen produced in reforming is critical if, as is usually the case in an integrated refinery, the hydrogen produced is utilized in processes such as hydrotreating and hydrocracking, which require at least certain minimum partial pressures of hydrogen. If the purity becomes too low, the hydrogen can no longer be used for this purpose and must be used in a less valuable way, for example as fuel gas.

FEEDSTOCK

Regarding the acyclic hydrocarbons that are subjected to the method of the present invention, they are most commonly paraffins but can in general be any acyclic hydrocarbon capable of undergoing ring-closure to produce an aromatic hydrocarbon. That is, it is intended to include within the scope of the present invention, the dehydrocyclization of any acyclic hydrocarbon capable of undergoing ring-closure to produce an aromatic hydrocarbon and capable of being vaporized at the dehydrocyclization temperatures used herein. More particularly, suitable acyclic hydrocarbons include acyclic hydrocarbons containing 6 or more carbon atoms per molecule such as $C_6$-$C_{20}$ paraffins, and $C_6$-$C_{20}$ olefins. Specific examples of suitable acyclic hydrocarbons are: (1) paraffins such as n-hexane, 2-methylpentane, 3-methylpentane, n-heptane, 2-methylhexane, 3-methylhexane, 3-ethylpentane, 2,5-dimethylhexane, n-octane, 2-methylheptane, 3-methylheptane, 4-methylheptane, 3-ethylhexane, n-nonane, 2-methyloctane, 3-methyloctane, n-decane and the like compounds; and (2) olefins such as 1-hexene, 2-methyl-1-pentene, 1-heptene, 1-octene, 1-nonene and the like compounds.

In a preferred embodiment, the acyclic hydrocarbon is a paraffinic hydrocarbon having about 6 to 10 carbon atoms per molecule. It is to be understood that the specific acyclic hydrocarbons mentioned above can be charged to the present method individually, in admixture with one or more of the other acyclic hydrocarbons, or in admixture with other hydrocarbons such as naphthenes, aromatics and the like. Thus mixed hydrocarbon fractions, containing significant quantities of acyclic hydrocarbons that are commonly available in a typical refinery, are suitable charge stocks for the instant method; for example, highly paraffinic straight-run naphthas, paraffinic raffinates from aromatic extraction or adsorption, $C_6$-$C_9$ paraffin-rich streams and the like refinery streams. An especially preferred embodiment involves a charge stock which is a paraffin-rich naphtha fraction boiling in the range of about 140° F. to about 350° F. Generally, best results are obtained with a charge stock comprising a mixture of $C_6$-$C_{10}$ paraffins, especially $C_6$-$C_8$ paraffins.

Preferably, the feedstock is substantially free of sulfur, nitrogen, metals, and other known poisons for reforming catalysts. This catalyst is especially sensitive to sulfur. The feedstock can be made substantially free of sulfur, nitrogen, metals, and other known poisons by conventional hydrofining techniques plus sorbers that remove sulfur compounds.

In the case of a feedstock which is not already low in sulfur, acceptable levels can be reacted by hydrofining the feedstock in a pretreatment zone where the naphtha is contacted with a hydrofining catalyst which is resistant to sulfur poisoning. A suitable catalyst for this hydrodesulfurization process is, for example, an alumina-containing support and a minor proportion of molybdenum oxide, cobalt oxide and/or nickel oxide. Hydrodesulfurization is ordinarily conducted at 315° C. to 455° C., at 200 to 2000 psig, and at a liquid hourly space velocity of 1 to 5. The sulfur and nitrogen contained in the naphtha are converted to hydrogen sulfide and ammonia, respectively, which can be removed prior to reforming by suitable conventional processes.

DEHYDROCYCLIZATION REACTION

According to the present invention, the acyclic hydrocarbon is contacted with the catalyst in a dehydrocyclization zone maintained at dehydrocyclization conditions. This contacting may be accomplished by using the catalyst in a fixed bed system, a moving bed system, a fluidized system, or in a batch-type operation; however, in view of the danger of attrition losses of the valuable catalyst and of well-known operational advantages, it is preferred to use either a fixed bed system or a denser-phase moving bed system. It is also contemplated that the contacting step can be performed in the presence of a physical mixture with particles of a conventional dual-function catalyst of the prior art. In a fixed bed system, the acyclic hydrocarbon-containing charge stock is preheated by any suitable heating means to the desired reaction temperature and then passed into a dehydrocyclization zone containing a fixed bed of the catalyst. It is, of course, understood that the dehydrocyclization zone may be one or more separate reactors with suitable means therebetween to ensure that the desired conversion temperature is maintained at the entrance to each reactor. It is also important to note that the reactants may be contacted with the catalyst bed in either upward, downward, or radial flow fashion. In addition, the reactants may be in a liquid phase, a mixed liquid-vapor phase, or a vapor phase when they contact the catalyst, with best results obtained in the vapor phase. The dehydrocyclization system then preferably comprises a dehydrocyclization zone containing one or more fixed beds or dense-phase moving beds of the catalyst. In a multiple bed system, it is, of course, within the scope of the present invention to use the present catalyst in less than all of the beds with a conventional dual-function catalyst being used in the remainder of the beds. The dehydrocyclization zone may be one or more separate reactors with suitable heating means therebetween to compensate for the endothermic nature of the dehydrocyclization reaction that takes place in each catalyst bed.

Although hydrogen is the preferred diluent for use in the subject dehydrocyclization method, in some cases other art-recognized diluents may be advantageously utilized, either individually or in admixture with hydrogen, such as $C_1$ to $C_5$ paraffins such as methane, ethane, propane, butane and pentane; the like diluents, and mixtures thereof. Hydrogen is preferred because it serves the dual function of not only lowering the partial pressure of the acyclic hydrocarbon, but also of suppressing the formation of hydrogen-deficient, carbonaceous deposits (commonly called coke) on the catalytic composite. Ordinarily, hydrogen is utilized in amounts sufficient to insure a hydrogen to hydrocarbon mole ratio of about 0 to about 20:1, with best results obtained in the range of about 2:1 to about 6:1. The hydrogen charged to the dehydrocyclization zone will typically be contained in a hydrogen-rich gas stream recycled from the effluent stream from this zone after a suitable gas/liquid separation step.

The hydrocarbon dehydrocyclization conditions used in the present method include a reactor pressure which is selected from the range of about 1 atmosphere to about 500 psig, with the preferred pressure being about 50 psig to about 200 psig. The temperature of the dehydrocyclization is preferably about 450° C. to about 550° C. As is well known to those skilled in the dehydrocyclization art, the initial selection of the temperature within this broad range is made primarily as a function of the desired conversion level of the acyclic hydrocarbon considering the characteristics of the charge stock and of the catalyst. Ordinarily, the temperature then is thereafter slowly increased during the run to compensate for the inevitable deactivation that occurs to provide a relatively constant value for conversion.

The liquid hourly space velocity (LHSV) used in the instant dehydrocyclization method is selected from the range of about 0.1 to about 10 hr.$^{-1}$, with a value in the range of about 0.3 to about 5 hr.$^{-1}$ being preferred.

Reforming generally results in the production of hydrogen. Thus, exogenous hydrogen need not necessarily be added to the reforming system except for prereduction of the catalyst and when the feed is first introduced. Generally, once reforming is underway, part of the hydrogen produced is recirculated over the catalyst. The presence of hydrogen serves to reduce the formation of coke which tends to poison the catalyst. Hydrogen is preferably introduced into the reforming reactor at a rate varying from 0 to about 20 moles of hydrogen per mole of feed. The hydrogen can be in admixture with light gaseous hydrocarbons.

If, after a period of operation, the catalyst has become deactivated by the presence of carbonaceous deposits, said deposits can be removed from the catalyst by passing an oxygen-containing gas, such as dilute air, into contact with the catalyst at an elevated temperature in order to burn the carbonaceous deposits from the catalyst. The regeneration can be performed either in the semiregenerative mode in which the reforming operation is interrupted after a more or less long period of time and catalyst regeneration is carried out, or in the onstream regenerative mode, in which a portion of the catalyst is regenerated while the reforming operation is continued over the remainder of the catalyst. Two types of onstream regeneration are known in the prior art, cyclic and continuous reforming. In cyclic reforming, the catalyst in one of a series of reactors is regenerated while reforming is continued in the rest of the plant. In continuous reforming, a portion of deactivated catalyst is removed from the plant, regenerated in a separate regeneration system while reforming is continued in the plant, and the regenerated catalyst is returned to the plant. The method of regenerating the catalyst will depend on whether there is a fixed bed, moving bed, or fluidized bed operation. Regeneration methods and conditions are well known in the art.

THE CATALYST

The catalyst according to the invention is a type L zeolite charged with a Group VIII metal and an alkaline earth metal.

TYPE L ZEOLITE

Type L zeolites are synthetic zeolites. A theoretical formula is $M_{9/n}[(AlO_2)_9(SiO_2)_{27}]$ in which M is a cation having the valency n.

The real formula may vary without changing the crystalline structure; for example, the mole ratio of silicon to aluminum (Si/Al) may vary from 1.0 to 3.5.

Although there are a number of cations that may be present in zeolite L, in one embodiment, it is preferred to synthesize the potassium form of the zeolite, i.e., the form in which the exchangeable cations present are substantially all potassium ions. The reactants accordingly employed are readily available and generally water soluble. The exchangeable cations present in the zeolite may then conveniently be replaced by other exchangeable cations, as will be shown below, thereby yielding isomorphic form of zeolite L.

In one method of making zeolite L, the potassium form of zeolite L is prepared by suitably heating an aqueous metal aluminosilicate mixture whose composition, expressed in terms of the mole ratios of oxides, falls within the range:

| | |
|---|---|
| $K_2O/(K_2O + Na_2O)$ | From about 0.33 to about 1 |
| $(K_2O + Na_2O)/SiO_2$ | From about 0.35 to about 0.5 |
| $SiO_2/Al_2O_3$ | From about 10 to about 28 |
| $H_2O/(K_2O + Na_2O)$ | From about 15 to about 41 |

The desired product is hereby crystallized out relatively free from zeolites of dissimilar crystal structure.

The potassium form of zeolite L may also be prepared in another method along with other zeolitic compounds by employing a reaction mixture whose composition, expressed in terms of mole ratios of oxides, falls within the following range:

| | |
|---|---|
| $K_2O/(K_2O + Na_2O)$ | From about 0.26 to about 1 |
| $(K_2O + Na_2O)/SiO_2$ | From about 0.34 to about 0.5 |
| $SiO_2/Al_2O_3$ | From about 15 to about 28 |
| $H_2O/(K_2O + Na_2O)$ | From about 15 to about 51 |

It is to be noted that the presence of sodium in the reaction mixture is not critical to the present invention.

When the zeolite is prepared from reaction mixtures containing sodium, sodium ions are generally also included within the product as part of the exchangeable cations together with the potassium ions. The product obtained from the above ranges has a composition, expressed in terms of moles of oxides, corresponding to the formula:

$$0.9\text{-}1.3[(1-x)K_2O, xNa_2O]:Al_2O_3:5.2\text{-}6.9SiO_2:yH_2O$$

wherein "x" may be any value from 0 to about 0.75 and "y" may be any value from 0 to about 9.

In making zeolite L, representative reactants are activated alumina, gamma alumina, alumina trihydrate and sodium aluminate as a source of alumina. Silica may be obtained from sodium or potassium silicate, silica gels, silicic acid, aqueous colloidal silica sols and reactive amorphous solid silicas. The preparation of typical silica sols which are suitable for use in the process of the present invention are described in U.S. Pat. Nos. 2,574,902 and 2,597,872. Typical of the group of reactive amorphous solid silicas, preferably having an ultimate particle size of less than 1 micron, are such materials as fume silicas, chemically precipitated and precipitated silica sols. Potassium and sodium hydroxide may supply the metal cation and assist in controlling pH.

In making zeolite L, the usual method comprises dissolving potassium or sodium aluminate and alkali, viz., potassium or sodium hydroxide, in water. This solution is admixed with a water solution of sodium silicate, or preferably with a water-silicate mixture derived at least in part from an aqueous colloidal silica sol. The resultant reaction mixture is placed in a container made, for example, of metal or glass. The container should be closed to prevent loss of water. The reaction mixture is then stirred to insure homogeneity.

The zeolite may be satisfactorily prepared at temperatures of from about 90° C. to 200° C. the pressure being atmospheric or at least that corresponding to the vapor pressure of water in equilibrium with the mixture of reactants at the higher temperature. Any suitable heating apparatus, e.g., an oven, sand bath, oil bath or jacketed autoclave, may be used. Heating is continued until the desired crystalline zeolite product is formed. The zeolite crystals are then filtered off and washed to separate them from the reactant mother liquor. The zeolite crystals should be washed, preferably with distillated water, until the effluent wash water, in equilibrium with the product, has a pH of between about 9 and 12. As the zeolite crystals are washed, the exchangeable cation of the zeolite may be partially removed and is believed to be replaced by hydrogen cations. If the washing is discontinued when the pH of the effluent wash water is between about 10 and 11, the $(K_2O+Na_2O)/Al_2O_3$ molar ratio of the crystalline product will be approximately 1.0. Thereafter, the zeolite crystals may be dried, conveniently in a vented oven.

Zeolite L has been characterized in "Zeolite Molecular Sieves" by Donald W. Breck, John Wiley & Sons, 1974, as having a framework comprising 18 tetrahedra unit cancrinite-type cages linked by double 6-rings in columns and crosslinked by single oxygen bridges to form planar 12-membered rings. These 12-membered rings produce wide channels parallel to the c-axis with no stacking faults. Unlike erionite and cancrinite, the cancrinite cages are symmetrically placed across the double 6-ring units. There are four types of cation locations: A in the double 6-rings, B in the cancrinite-type cages, C between the cancrinite-type cages, and D on the channel wall. The cations in site D appear to be the only exchangeable cations at room temperature. During dehydration, cations in site D probably withdraw from the channel walls to a fifth site, site E, which is located between the A sites. The hydrocarbon sorption pores are approximately 7 to 8 Angstroms in diameter.

A more complete description of these zeolites is given, e.g., in U.S. Pat. No. 3,216,789 which, more particularly, gives a conventional description of these zeolites. U.S. Pat. No. 3,216,789 is hereby incorporated by reference to show a type L zeolite useful in the present invention.

Zeolite L is a large pore zeolite (zeolites having a pore size of at least 6 Angstroms). Other large pore zeolites include A, X, Y, omega and mordenite. Zeolite L differs from these other large pore zeolites in a variety of ways, besides X-ray diffraction pattern.

One of the most pronounced differences is in the channel system of zeolite L. Zeolite L has a one-dimensional channel system parallel to the c-axis, while most other zeolites have either two-dimensional or three-dimensional channel systems. Zeolite A, X and Y all have three-dimensional channel systems. Mordenite (Large Port) has a major channel system parallel to the c-axis, and another very restricted channel system parallel to the b-axis. Omega zeolite has a one-dimensional channel system.

Another pronounced difference is in the framework of the various zeolites. Only zeolite L has cancrinite-type cages linked by double-six rings in columns and crosslinked by oxygen bridges to form planar 12-rings. Zeolite A has a cubic array of truncated octahedra, beta-cages linked by double-four ring units. Zeolites X and Y both have truncated octahedra, beta-cages, linked tetrahedrally through double-six rings in an arrangement like carbon atoms in a diamond. Mordenite has complex chains of five-rings crosslinked by four-ring chains. Omega has a fourteen-hedron of gmelinite-type linked by oxygen bridges in columns parallel to the c-axis.

Presently, it is not known which of these differences, or other differences, is responsible for the high selectively for dehydrocyclization of catalysts made from zeolite L, but it is known that catalysts made of zeolite L do react differently than catalysts made of other zeolites.

Various factors have an effect on the X-ray diffraction pattern of a zeolite. Such factors include temperature, pressure, crystal size, impurities, and type of cations present. For instance, as the crystal size of the type L zeolite becomes smaller, the X-ray diffraction pattern becomes broader and less precise. Thus, the term "zeolite L" includes any zeolites made up of cancrinite cages having an X-ray diffraction pattern substantially similar to the X-ray diffraction patterns shown in U.S. Pat. No. 3,216,789.

Crystal size also has an effect on the stability of the catalyst. For reasons not yet fully understood, catalysts having at least 80% of the crystals of the type L zeolite larger than 1000 Angstroms give longer run length than catalysts having substantially all of the crystals of the type L zeolite between 200 and 500 Angstroms. Thus, the larger of these crystallite sizes of type L zeolite is the preferred support.

Type L zeolites are conventionally synthesized largely in the potassium form, i.e., in the theoretical formula given previously, most of the M cations are potassium. The M cations are exchangeable, so that a given type L zeolite, e.g., a type L zeolite in the potassium form, can be used to obtain type L zeolites containing other cations, by subjecting the type L zeolite to ion exchange treatment in an aqueous solution of appropriate salts. However, it is difficult to exchange all of the original cations, e.g., potassium, since some exchangeable cations in the zeolite are in sites which are difficult for the reagents to reach.

ALKALINE EARTH METALS

An essential element of the present invention is the presence of an alkaline earth metal in the type L zeolite. That alkaline earth metal must be either barium, strontium or calcium. Preferably the alkaline earth metal is barium. The alkaline earth metal can be incorporated into the zeolite by synthesis, impregnation or ion exchange. Barium is preferred to the other alkaline earths because the resulting catalyst has high activity, high selectivity and high stability.

In one embodiment, at least part of the alkali metal is exchanged with barium, using techniques known for ion exchange of zeolites. This involves contacting the zeolite with a solution containing excess $Ba^{++}$ ions. The barium should preferably constitute from 0.1% to 35% of the weight of the zeolite, more preferably from 1% to 20% by weight.

GROUP VIII METALS

The catalysts according to the invention are charged with one or more Group VIII metals, e.g., nickel, ruthenium, rhodium, palladium, iridium or platinum.

The preferred Group VIII metals are iridium and particularly platinum, which are more selective with regard to dehydrocyclization and are also more stable under the dehydrocyclization reaction conditions than other Group VIII metals.

The preferred percentage of platinum in the catalyst is between 0.1% and 5%, more preferably from 0.1% to 1.5%.

Group VIII metals are introduced into the L zeolite by synthesis, impregnation or exchange in an aqueous solution of an appropriate salt. When it is desired to introduce two Group VIII metals into the zeolite, the operation may be carried out simultaneously or sequentially.

By way of example, platinum can be introduced by impregnating the zeolite with an aqueous solution of tetrammineplatinum (II) nitrate, tetrammineplatinum (II) hydroxide, dinitrodiamino-platinum or tetrammineplatinum (II) chloride. In an ion exchange process, platinum can be introduced by using cationic platinum complexes such as tetrammineplatinum (II) nitrate.

CATALYST PELLETS

An inorganic oxide can be used as a carrier to bind the type L zeolite containing the Group VIII metal and alkaline earth metal and give the catalyst additional strength. The carrier can be a natural or a synthetically produced inorganic oxide or combination of inorganic oxides. Preferred loadings of inorganic oxide are from 5% to 25% by weight of the catalyst. Typical inorganic oxide supports which can be used include aluminosilicates (such as clays), alumina, and silica, in which acidic sites are preferably exchanged by cations which do not impart strong acidity.

One preferred inorganic oxide support is attapulgite. Another preferred inorganic oxide support is "Ludox", which is a colloidal suspension of silica in water, stabilized with a small amount of alkali.

When an inorganic oxide is used as a carrier, there are two preferred methods in which the catalyst can be made, although other embodiments could be used.

In the first preferred embodiment, the type L zeolite is made, then the type L zeolite is ion exchanged with a barium solution, separated from the barium solution, dried and calcined, impregnated with platinum, calcined, and then mixed with the inorganic oxide and extruded through a die to form cylindrical pellets. Advantageous methods of separating the type L zeolite from the barium and platinum solutions are by a batch centrifuge or a pressed filter. This embodiment has the advantage that all the barium and platinum are incorporated on the type L zeolite and none are incorporated on the inorganic oxide. It has the disadvantage that the type L zeolite is of small size, which is hard to separate from the barium solution and the platinum solution.

In the second preferred embodiment, the type L zeolite is mixed with the inorganic oxide and extruded through the die to form cylindrical pellets, then these pellets are ion exchanged with a barium solution, separated from the barium solution, impregnated with platinum, separated from the platinum solution, and calcined. This embodiment has the advantage that the pellets are easy to separate from the barium and platinum solutions, but it has the disadvantage that barium and platinum may be also deposited on the inorganic oxide carrier which could catalyze undesirable reactions. Thus, the choice of which embodiment is used depends on the trade-off between catalyst selectivity and ease of separation of the catalyst from the barium and platinum solutions.

In the extrusion of type L zeolite, various extrusion aids and pore formers can be added. Examples of suitable extrusion aids are ethylene glycol and stearic acid. Examples of suitable pore formers are wood flour, cellulose and polyethylene fibers.

After the desired Group VIII metal or metals have been introduced, the catalyst is treated in air at about 260° C. and then reduced in hydrogen at temperatures of from 200° C. to 700° C., preferably 300° C. to 620° C.

At this stage the catalyst is ready for use in the dehydrocyclization process. In some cases however, for example when the metal or metals have been introduced by an ion exchange process, it is preferable to eliminate any residual acidity of the zeolite by treating the catalyst with an aqueous solution of a salt of a suitable alkali or alkaline earth element in order to neutralize any hydrogen ions formed during the reduction of metal ions by hydrogen.

In order to obtain optimum selectivity, temperature should be adjusted so that reaction rate is appreciable, but conversion is less than 98%, as excessive temperature and excess reaction can have an adverse affect on selectivity. Pressure should also be adjusted within a proper range. Too high a pressure will place a thermodynamic (equilibrium) limit on the desired reaction, especially for hexane aromatization, and too low a pressure may result in coking and deactivation.

Although the primary benefit of this invention is in improving the selectivity for conversion of acyclic hydrocarbons (especially $C_6$–$C_8$ paraffins) to aromatics, it is also surprisingly found that the selectivity for conversion of methylcyclopentane to benzene is excellent. This reaction, which on conventional reforming catalysts based on chlorided alumina involves an acid catalyzed isomerization step, occurs on the catalyst of this invention with selectivity as good as or better than on the chlorided alumina based catalysts of the prior art. Thus, the present invention can also be used to catalyze the conversion of stocks high in 5-membered-ring alkyl naphthenes to aromatics.

Another advantage of this invention is that the catalyst of the present invention is more stable than prior art zeolitic catalysts. Stability of the catalyst, or resistance to deactivation, determines its useful run length. Longer run lengths result in less down time and expense in regenerating or replacing the catalyst charge.

EXAMPLES

The invention will be further illustrated by the following examples which set forth a particularly advantageous method and composition embodiments. While the examples are provided to illustrate the present invention, they are not intended to limit it.

EXAMPLE I

An Arabian Light straight run naphtha which had been hydrofined to remove sulfur, oxygen and nitrogen was reformed at 100 psig, 2 LHSV, and 6 $H_2/HC$ by three different catalysts. The feed contained 80.2 v % paraffins, 16.7 v % naphthenes, and 3.1 v % aromatics, and it contained 21.8 v % $C_5$, 52.9 v % $C_6$, 21.3 v % $C_7$, and 3.2 v % $C_8$.

In the first run, the Arabian Light straight run naphtha was reformed at 499° C. using a commercial sulfided platinum-rhenium-alumina catalyst prepared as disclosed in U.S. Pat. No. 3,415,737.

In the second run, the Arabian Light straight run naphtha was reformed at 493° C. using a platinum-potassium-type L zeolite catalyst formed by: (1) impregnating a potassium-type L zeolite having crystal sizes of from about 1000 to 4000 Angstroms containing 0.8% platinum impregnated as tetrammineplatinum (II) nitrate; (2) drying the catalyst; (3) calcining the catalyst at 260° C.; and (4) reducing the catalyst in hydrogen at 480° C. to 500° C. for 1 hour.

In the third run, the process of the present invention, the Arabian Light straight run naphtha was reformed at 493° C. using a platinum-barium-type L zeolite catalyst formed by: (1) ion exchanging a potassium-type L zeolite having crystal sizes of from about 1000 to 4000 Angstroms with a sufficient volume of 0.17 molar barium nitrate solution to contain an excess of barium compared to the ion exchange capacity of the zeolite; (2) drying the resulting barium-exchanged type L zeolite catalyst; (3) calcining the catalyst at 590° C.; (4) impregnating the catalyst with 0.8% platinum using tetrammineplatinum (II) nitrate; (5) drying the catalyst; (6) calcining the catalyst at 260° C.; and (7) reducing the catalyst in hydrogen at 480° C. to 500° C. for 1 hour.

The results of these three runs are shown in Table I.

TABLE I

|  | Feed | 499° C. Pt/Re/ Alumina | 493° C. Pt/K/L | 493° C. Pt/Ba/L |
|---|---|---|---|---|
| $C_1$ Wt % Fd |  | 2.8 | 5.5 | 3.6 |
| $C_2$ |  | 6.6 | 2.5 | 1.3 |
| $C_3$ |  | 9.3 | 3.2 | 1.5 |
| $iC_4$ | 0.1 | 5.8 | 0.9 | 0.5 |
| $NC_4$ | 0.5 | 6.8 | 3.8 | 2.4 |
| $iC_5$ | 5.1 | 13.6 | 6.7 | 5.6 |
| $NC_5$ | 11.3 | 9.8 | 12.6 | 12.6 |
| $C_6$+ P + N | 81.3 | 13.4 | 7.8 | 9.3 |
| Benzene | 1.5 | 15.1 | 40.6 | 43.8 |
| $C_7$+ Aromatics | .8 | 15.8 | 12.7 | 15.0 |
| $C_5$+ LV % Yield |  | 63 | 69.9 | 74.4 |
| Hydrogen, SCF/B |  | 470 | 1660 | 2050 |
| Selectivity, Mole % |  | 20 | 72 | 87 |

TABLE I-continued

|  | Feed | 499° C. Pt/Re/ Alumina | 493° C. Pt/K/L | 493° C. Pt/Ba/L |
|---|---|---|---|---|
| $C_6$+ P → Aromatics |  |  |  |  |

This series of runs shows that the use of a platinum-barium-type L zeolite catalyst in reforming gives a selectivity for converting hexanes to benzene markedly superior to that of the prior art. Notice that associated with this superior selectivity is an increased production of hydrogen gas, which can be used in other processes. Notice also that the hydrogen purity is higher for the Pt/Ba/L run since more hydrogen is produced and less $C_1$ p us $C_2$ are produced.

EXAMPLE II

A second series of runs was made using hydrofined n-hexane as feed. All runs in this series were made at 490° C., 100 psig, 3 LHSV and 3 $H_2/HC$.

In the first run, a platinum-potassium-type L zeolite was used which had been prepared by the procedures shown in the second process of Example I.

In the second run, a platinum-barium-type L zeolite was used which had been prepared by the procedures shown in the third run of Example I except that the barium nitrate solution was 0.3 molar instead of 0.17 molar. The results of these runs are given below in Table II.

TABLE II

|  | Conversion | | Selectivity for n-hexane | |
|---|---|---|---|---|
|  | 5 Hrs. | 20 Hrs. | 5 Hrs. | 20 Hrs. |
| Pt/K/L | 70 | 59 | 76 | 79 |
| Pt/Ba/L | 85 | 85 | 89 | 92 |

Thus, in operation, the incorporation of barium into type L zeolite causes a dramatic improvement in selectivity for n-hexane. Notice that the stability of the platinum-barium-type L zeolite is excellent. After 20 hours, there was no drop in conversion when platinum-barium-type L zeolite catalyst was used.

EXAMPLE III

A third series of runs was made using different cation exchanges. All runs in this series were made at 490° C., 100 psig, and 6 $H_2/HC$. The feed which was hydrofined, contained 80.9 v % paraffins, 16.8 v % naphthenes, 1.7 v % aromatics, 0.4 v % olefins and it contained 2.6 v % $C_5$, 47.6 v % $C_6$, 43.4 v % $C_7$ and 6.3 v % $C_8$ hydrocarbons.

In the first run, a platinum-barium-type L zeolite was used which had been prepared by the same procedures shown in the second run of Example II. It was tested at an LHSV of 2.0.

In the second run, a platinum-calcium-type L zeolite was used which had been prepared by the same procedures except that a 0.3 molar calcium nitrate solution was used. It was tested at an LHSV of 2.0.

In the third run, a platinum-strontium-type L zeolite was used which had been prepared by the same procedures except that a 0.3 molar strontium nitrate solution was used in the exchange. It was tested at an LHSV of 2.0.

In the fourth run, a platinum-cesium-type L zeolite was used which had been prepared by the same procedures except that a 0.3 molar cesium nitrate solution was used in the exchange. It was tested at an LHSV of 2.0.

In the fifth run, a platinum-barium-type L zeolite was used which had been prepared by the same procedures as the first run. It was tested at an LHSV of 6.0.

In the sixth run, a platinum-potassium-type L zeolite was used which had been prepared by the procedures shown in the second process of Example I. It was tested at an LHSV of 6.0.

In the seventh run, a platinum-rubidium-type L zeolite was used which had been prepared by the procedures of the first run except that a 0.3 molar rubidium nitrate solution was used in the exchange. It was tested at 6.0 LHSV.

In the eighth run, a platinum-lanthanum-type L zeolite was used which had been prepared by the procedures of the first run except that a 0.3 molar lanthanum nitrate solution was used in the exchange. It was tested at 6.0 LHSV.

In the ninth run, a platinum-magnesium type L zeolite was used which had been prepared by the procedures of the first run except that a 0.3 molar magnesium nitrate solution was used in the exchange. It was tested at 6.0 LHSV.

In the tenth run, a platinum-lithium type L zeolite was used which had been prepared by the procedures of the first run except that a 0.3 molar lithium nitrate solution was used in the exchange. It was tested at 6.0 LHSV.

In the eleventh run, a platinum-sodium type L zeolite was used which had been prepared by the procedures of the first run except that a 0.3 molar sodium nitrate solution was used in the exchange. It was tested at 6.0 LHSV. The results of all eleven runs are shown in Table III.

TABLE III

|  | Paraffin Conversion | | Selectivity Mole % | | Aromatics Mole % Feed | |
|---|---|---|---|---|---|---|
|  | 3 hrs. | 20 hrs. | 3 hrs. | 20 hrs. | 3 hrs. | 20 hrs. |
| 2.0 LHSV | | | | | | |
| Pt/Ba/L | 87 | 87 | 83 | 85 | 75 | 76 |
| Pt/Ca/L | 96 | 93 | 63 | 70 | 65 | 70 |
| Pt/Sr/L | 92 | 83 | 61 | 69 | 62 | 63 |
| Pt/Cs/L | 84 | 73 | 73 | 75 | 66 | 61 |
| 6.0 LHSV | | | | | | |
| Pt/Ba/L | 73 | 63 | 80 | 83 | 64 | 59 |
| Pt/K/L | 75 | 66 | 71 | 75 | 60 | 57 |
| Pt/Rb/L | 84 | 74 | 72 | 77 | 65 | 63 |
| Pt/La/L | 63 | 55 | 63 | 58 | 50 | 48 |
| Pt/Mg/L | 23 | <5 | 23 | — | 22 | 14 |
| Pt/Li/L | 77 | 72 | 70 | 74 | 61 | 60 |
| Pt/Na/L | 74 | 67 | 72 | 75 | 60 | 58 |

Thus, in operation, the incorporation of barium into type L zeolites causes a dramatic improvement in selectivity over type L zeolites having other cations (more than 25% reduction in the amount of cracked products produced for L zeolite having any other cation).

EXAMPLE IV

A platinum-barium-type L zeolite was used in two runs which had been prepared by the procedures shown in the second run of Example II. In the first run, the L zeolite crystallite size was about 1000 to 2000 Angstroms by transmission electron microscopy. In the second run, the L zeolite crystallite size was about 400 Angstroms. The feed of both runs contained 70.2 v % paraffins, 24.6 v % naphthenes, 5.0 v % aromatics, and 29.7 v % $C_5$'s, 43.4 v % $C_6$'s, 21.2 v % $C_7$'s, 5.0 v % $C_8$'s, 0.6 v % $C_9$'s. Research octane clear of the feed was 71.4. The catalyst of the first run was reduced in hydrogen for 20 hours at 1050° F. The catalyst of the second run was reduced in hydrogen for 2 hours at 1050° F. The run conditions were 100 psig, 1.5 LHSV, and 6.0 $H_2$/HC recycle. The temperature was controlled to give 50 wt. % aromatics in the $C_5+$ liquid product, which corresponds to 89 research octane clear. The results of the first run are shown in Table IV.

TABLE IV

| Run Time, Hrs. | For 50 wt. % Aromatics Temperature °F. | $C_5+$ Yield LV % |
|---|---|---|
| 500 | 858 | 86.4 |
| 1000 | 868 | 86.2 |
| 2000 | 876 | 86.1 |
| 2500 | 880 | 86.2 |

The results of the second run are shown in Table V.

TABLE V

| Run Time, Hrs. | For 50 wt. % Aromatics Temperature °F. | $C_5+$ Yield LV % |
|---|---|---|
| 100 | 870 | 87 |
| 200 | 881 | 86 |
| 400 | 893 | 85 |

Thus, in operation, the large crystal size catalyst of the present invention gives exceptionally long run life, whereas the small crystal size catalyst deactivates much faster.

While the present invention has been described with reference to specific embodiments, this application is intended to cover those various changes and substitutions which may be made by those skilled in the art without departing from the spirit and scope of the appended claims.

What is claimed is:

1. A composition comprising:
   (a) an L zeolite;
   (b) at least one Group VIII metal; and
   (c) an alkaline earth metal selected from the group consisting of barium, strontium and calcium.

2. A composition according to claim 1 wherein said alkaline earth metal is barium and wherein said Group VIII metal is platinum.

3. A composition according to claim 2 wherein said composition has from 0.1% to 5% by weight platinum and from 0.1% to 35% by weight barium.

4. A composition according to claim 3 wherein said composition has from 0.1% to 1.5% by weight platinum and from 1% to 20% by weight barium.

5. A composition according to claim 4 wherein the majority of the crystals of said an L zeolite are larger than 500 Angstroms.

6. A composition according to claim 5 wherein the majority of the crystals of said an L zeolite are larger than 1000 Angstroms.

7. A composition according to claim 6 wherein at least 80% of the crystals of said an L zeolite are larger than 1000 Angstroms.

8. A composition according to claim 7 wherein said composition comprises:
   (a) an L zeolite containing from 0.1% to 1.5% by weight platinum and from 1% to 20% by weight barium; and
   (b) an inorganic binder.

9. A composition according to claim 8 wherein the inorganic binder is selected from the group consisting of silica, alumina, and aluminosilicates.

10. A composition consisting essentially of:
    (a) an L zeolite which contains at least one alkali metal;
    (b) an inorganic oxide binder;
    (c) platinum; and
    (d) barium.

11. A composition according to claim 10 wherein said composition has from 0.1% to 5% by weight platinum and 0.1% to 35% by weight barium.

12. A composition according to claim 11 wherein said composition has from 0.1% to 1.5% by weight platinum and from 1% to 20% by weight barium.

13. A composition according to claim 12 wherein the majority of the crystals of said an L zeolite are larger than 500 Angstroms.

14. A composition according to claim 13 wherein the majority of the crystals of said an L zeolite are larger than 1000 Angstroms.

15. A composition according to claim 14 wherein at least 80% of the crystals of said an L zeolite are larger than 1000 Angstroms.

16. A composition according to claim 15 wherein said composition consists essentially of:
    (a) an L zeolite containing at least one alkali metal, from 0.1% to 1.5% by weight platinum and from 1% to 20% by weight barium; and
    (b) an inorganic binder.

17. A composition according to claim 16 wherein the inorganic binder is selected from the group consisting of silica, alumina, and aluminosilicates.

18. A method of forming a reforming catalyst composition comprising:
    (a) ion exchanging an L zeolite containing potassium with a solution containing barium ions, wherein the sizes of substantially all of the crystals of said an L zeolite are at least 1000 Angstroms;
    (b) drying said ion exchanged an L zeolite;
    (c) calcining said dried an L zeolite;
    (d) impregnating said calcined an L zeolite with platinum;
    (e) drying said impregnated an L zeolite; and
    (f) calcining said dried impregnated an L zeolite.

19. A method of forming a reforming catalyst composition according to claim 18 wherein said solution containing barium ions is a barium nitrate solution and wherein said an L zeolite is impregnated in step (d) using tetrammineplatinum (II) nitrate.

* * * * *